United States Patent [19]

Kohno et al.

[11] Patent Number: 4,485,480

[45] Date of Patent: Nov. 27, 1984

[54] RADIATION IMAGE PHOTOGRAPHING APPARATUS

[75] Inventors: Hideki Kohno, Tokyo; Hidemi Shiono, Akikawa; Kensuke Sekihara, Tokyo; Shigenobu Yanaka; Takaji Suzuki, both of Kashiwa, all of Japan

[73] Assignee: Hitachi Medical Corporation, Tokyo, Japan

[21] Appl. No.: 366,781

[22] Filed: Apr. 8, 1982

[30] Foreign Application Priority Data

Apr. 10, 1981 [JP] Japan ................................. 56-53145

[51] Int. Cl.³ ............................................. G03B 41/16
[52] U.S. Cl. ......................................... 378/4; 378/22; 378/19
[58] Field of Search ........................ 378/22, 25, 26, 27, 378/2, 4, 9, 146, 19

[56] References Cited

U.S. PATENT DOCUMENTS 4,149,082  4/1979  Haendle ................................ 378/22
4,232,226 11/1980  Huettner .............................. 378/25

*Primary Examiner*—Craig E. Church
*Attorney, Agent, or Firm*—Antonelli, Terry & Wands

[57] ABSTRACT

A radiation-image photographing apparatus comprises a radiation source, a radiation detector disposed in opposition to the radiation source for detecting radiation through an object to be examined and to generate an electrical signal proportional to the amount of incident radiation, a scanning device for changing the relative, positional relationship between the radiation source and the radiation detector, an analog-to-digital converter for converting the output signal from the radiation detector to a digital quantity, a memory for storing the digital signal, an arithmetic unit, and a display unit. A plurality of measurements of a two-dimensional radiation absorption distribution of the object disposed between the radiation source and the radiation detector is obtained while the relative positional relationship between the radiation source and the radiation detector is being changed, and a linear arithmetic operation is performed on the plurality of image measurements, or a set of data passing a point within the object to be photographed, thereby displaying a cross-sectional image on a given cross-section approximately parallel to the radiation detector plane within the object to be examined.

4 Claims, 4 Drawing Figures

RADIATION IMAGE PHOTOGRAPHING APPARATUS

BACKGROUND OF THE INVENTION

This invention relates to an apparatus for obtaining, by using a radiation source and a radiation detector, the two-dimensional distribution of the transmission or absorption of a radiation to an object to be examined, and particularly to an apparatus so arranged that the radiation passed through the object is measured plural times while the relative, positional relation between the radiation source and radiation detector is being changed, and stored as digital images, and a linear arithmetic operation is performed on a set of data obtained from radiations passing a point within the object to be examined, thereby obtaining a cross-sectional image on a given cross-section approximately parallel to the radiation detector plane of the object to be examined.

The apparatus for photographing a cross-sectional image of human body by using radiation is well known. The conventional radiation cross-sectional image measuring apparatus photographs an image on a cross-section at a depth of human body by permitting usually a film to be exposed multiple times to the radiation of images while the relative positional relation between the radiation source and the radiation detector such as a film is being changed. This apparatus, however, obtains only a single cross-sectional image by a sequence of radiation emissions, and therefore for an unknown depth at which a focus exist, the human body is unnecessarily exposed to radiation.

SUMMARY OF THE INVENTION

It is an object of this invention to provide a radiation image photographing apparatus which has the above drawback obviated and is capable of obtaining an image on a cross-section of an object to be photographed, at a given detph parallel to the plane of a radiation detector, and a cross-sectional image on a cross-section of the object at a given depth paralled to the radiation detector plane.

In order to achieve the object of this invention, the images photographed while the relative positional relation between the radiation source and radiation detector is being changed are stored as digital images, and an arithmetic operation is performed on the digital images.

DESCRIPTION OF THE PREFERRED EMBODIMENT

Figure 1:
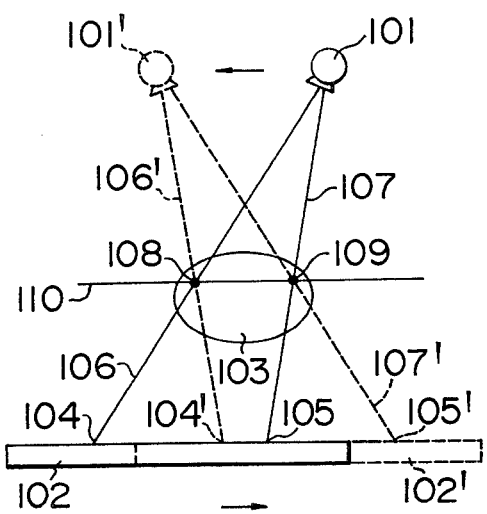
FIG. 1 is a diagram useful for explaining the principle of this invention.

FIG. 1 shows the principle of a cross-section photographing method. Although a one-dimensional spread of an X-ray is shown in FIG. 1 for simplicity of explanation, a two-dimensional spread of an X-ray is also obtainable for the method. Referring to FIG. 1, there are shown an X-ray tube 101, and an X-ray film 102. It is assumed that the X-ray tube 101 and the film 102 are linearly moved in synchronism with each other and arrive at positions 101' and 102' from the positions 101 and 102, respectively. The X-ray tube 101 continues to radiate the X-ray beam toward an object 103 to be examined, during its linear movement and as a result, the film 102 is exposed multiple times to the X-ray beam from the object 103 so that multiimages of the object 103 are recorded on the film 102. Now, let us consider X-ray beams 106 and 107 respectively arriving at positions 104 and 105 on the film 102. When the X-ray tube 101 and the film 102 arrive at the positions 101' and 102', respectively, the X-ray beams 106 and 107 are radiated in directions 106' and 107' as illustrated. In other words, while the X-ray tube 101 and the film 102 are being moved in the respective arrow-directions, the X-ray beams 106 and 107 always pass points 108 and 109 on the object 103 to be examined, respectively. Therefore, on the film 102, the information at the points 108 and 109 is added at all times during the linear movement of the X-ray tube 101, and that at the other points is shaded off. This condition is always satisfied at every point on a straight line 110, and thus the image taken on the film 102 is the information of the points on the straight line 110. If this principle is extended two-dimensionally, a cross-sectional image is photographed on the film.

Figure 2:
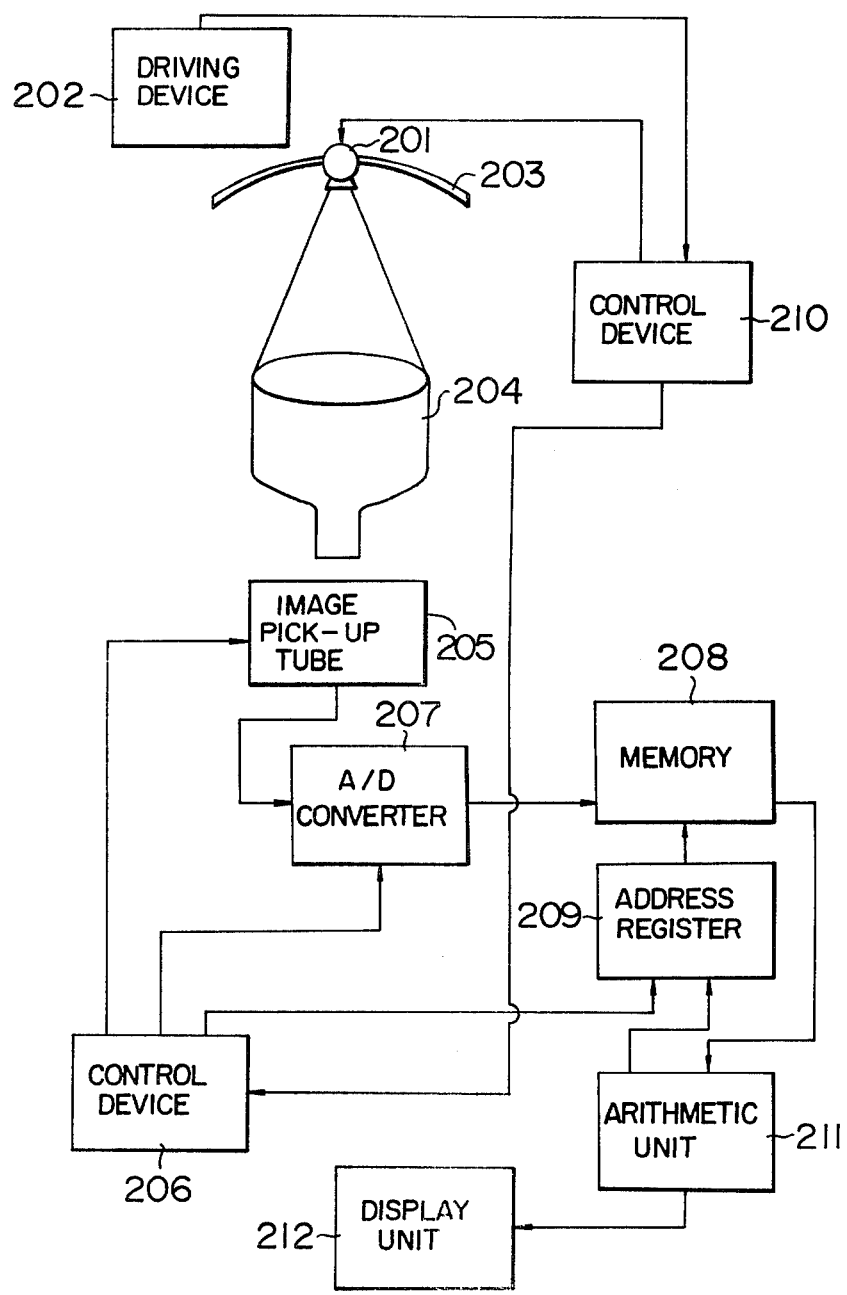
FIG. 2 is a block diagram of one embodiment of this invention.

FIG. 2 shows one embodiment of this invention. Referring to FIG. 2, there is shown a radiation generator 201, which is moved by a driving device 202 along a radiation generator track 203. An X-ray image intensifier (hereinafter, referred to as the X-ray I.I.) 204 serves to convert a radiation image to a light image. The object 103 to be examined (not shown) is disposed between the generator 201 and the X-ray I.I. 204. An image pick-up tube 205 serves to convert the output image from the X-ray I.I. 204 to an electrical signal. A control device 206 generates a signal necessary for scanning the screen of the pick-up tube 205 and at the same time supplies a control signal to an analog-to-digital converter 207 for converting the output signal from the pick-up tube 205 to a digital signal. The control device 206 also supplies a control signal to an address register 209 for permitting the output signal from the analog-to-digital converter 207 to be stored in a memory 208. A radiation emission control device 210 delivers an emission command to the radiation generator 201 and at the same time receives the output signal from the driving device 202 to monitor the position at which the radiation generator 201 is located. The control device 210 also supplies the generator-position signal to the control device 206. An arithmetic unit 211 processes the data stored in the memory 208 to obtain a cross-sectional image on any cross-section of the object to be examined and sends it to a display unit 212. If, now, the radiation generator 201 emits a radiative energy while moving along the track 203, and arrives at a predetermined position, the image is stored via the X-ray I.I. 204 and pick-up tube 205 in the memory 208. When the scanning is completed, the arithmetic unit 211 operates to calculate a cross-sectional image.

Figure 3:
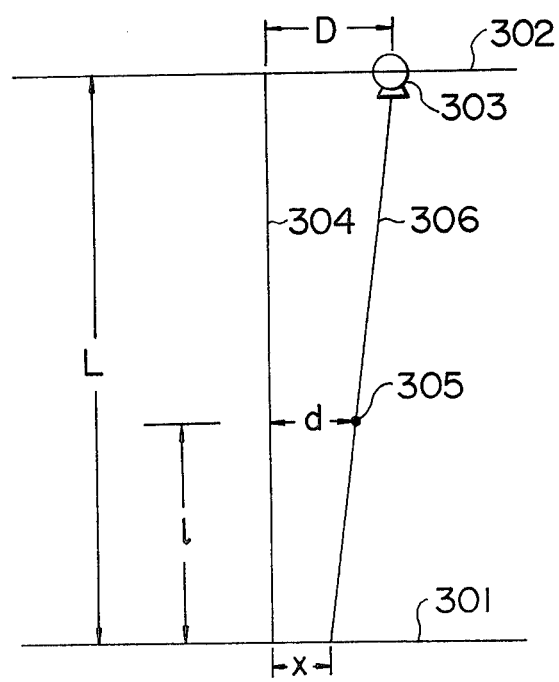
FIG. 3 is a diagram useful for explaining the operation of the embodiment in FIG. 2.

FIG. 3 is a diagram useful for explaining the way in which the arithmetic unit 211 in FIG. 2 processes the data. For simple explanation, a one-dimensional case is shown in FIG. 3, in which reference numeral 301 represents a plane of a radiation detector, and 302 a track along which a radiation source 303 moves, the track being a straight line located at a distance L from the radiation detector plane 301. If, now, the radiation source 303 is at a distance D from a center axis 304, a radiative beam 306 passing a point 305 which is distant by l from the radiation detector plane 301 and by d from the center axis 304 is incident to the detector plane 301 at a position which is away from the center axis by x, which is determined by $$x = (Ld - lD/L - l) \qquad (1)$$

Therefore, if for various different values of the distance D, the measured values at the positions of x determined by the above equation are added, it is possible to obtain the information in regard to the transmission or absorption of the radiation at point 305.

If under the condition of FIG. 3, the amount of the radiation beam which passes the point 305 and impinges at a point distance by x from the center axis 304 on the detector plane 301 is represented by f(x), the f(x) includes the information of radiation beams passing points other than the point 305. Thus, not only are added values of f(x) at different points of D, but using the neighboring or adjacent points, here $x + n \cdot \Delta x (n = \pm 1, \pm 2, \pm 3, \ldots)$ new amounts f'(x) of radiation is determined by $$f'(x) = \sum_{n=-N}^{N} W(n) \times f(x + n \cdot \Delta x) \qquad (2)$$

where W(n) is a function known as a diming correction weighting function. If values of f'(x) at different positions of D are added after calculation of the above equation, a cross-sectional image with less diming can be obtained by calculation. Therefore, the arithmetic unit 211 in FIG. 2, since it performs calculation of address, convolution and addition, can be realized with ease by a normal computer or special-purpose arithmetic unit. Although in FIG. 3 the radiation source is moved linearly, the same thing is true for arc-like movement of the radiation movement, and relative movement between the radiation source and detector.

Figure 4:
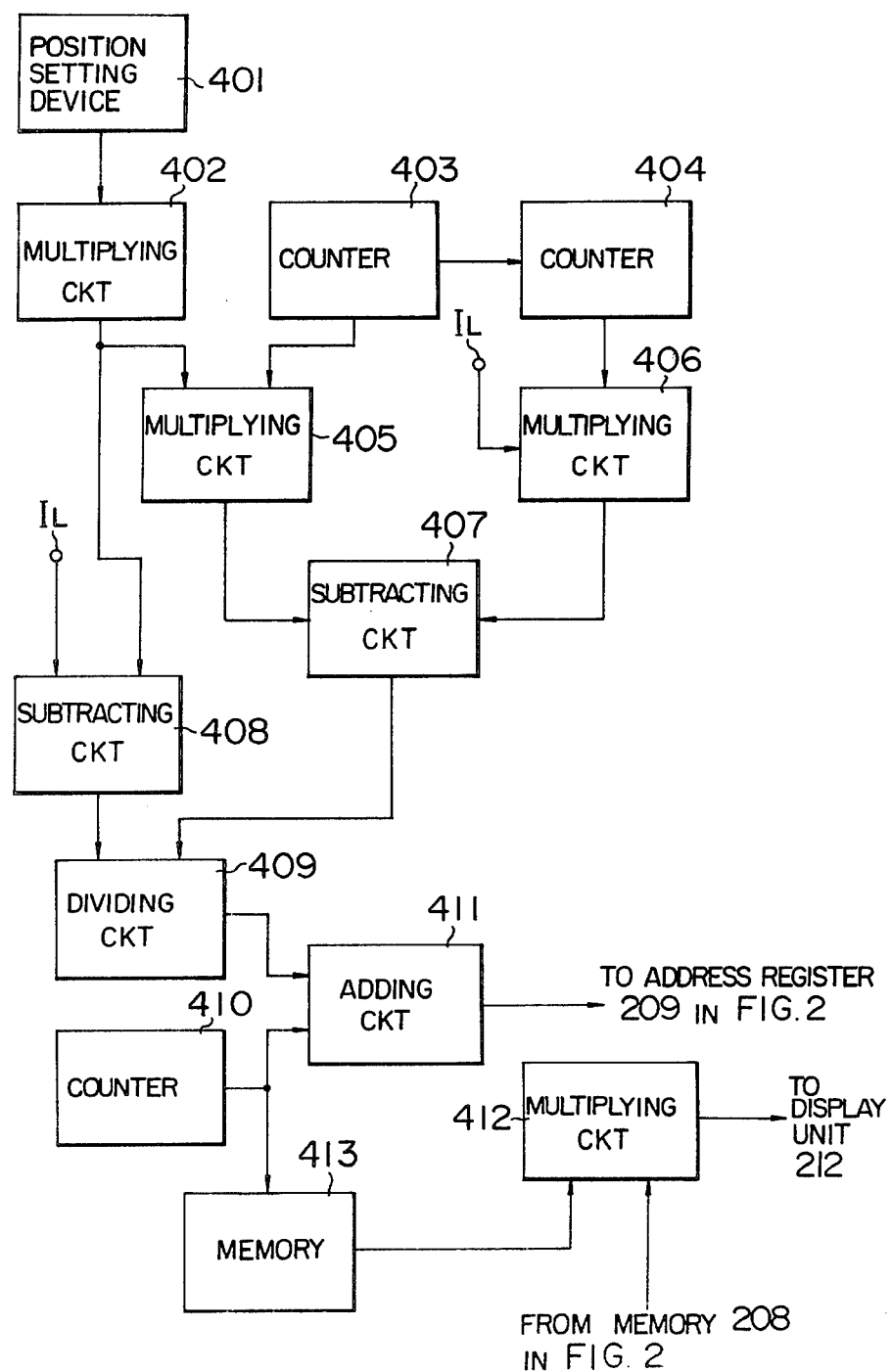
FIG. 4 is a block diagram of an example of a main part of the arrangement of FIG. 2.

FIG. 4 is a block diagram of an embodiment of the arithmetic unit 211 in FIG. 2. In FIG. 4, a position setting device 401 is formed of, for example, a digital switch to specify the position l on a cross-sectional plane in Eq. (1). A mutliplying circuit 402 for multiplying the position l by a predetermined factor converts an amount of the l in actual space to a digital value. This multiplying circuit 402 includes a factor generator. Counters 403 and 404 provide values of D and d in Eq. (1). A multiplying circuit 405 calculates l·D, and a multiplying circuit 406 calculates L·d. A subtracting circuit 407 is supplied with input signals of L·d and l·D and produces the result of calculation, L·d − l·D. A subtracting circuit 408 subtracts value of l from constant value of L. A dividing circuit 409 is supplied with input signals of the values (Ld−lD) and (L−l) and calculates x of Eq. (1). A counter 410 produces n·Δx for the calculation of (x+n·Δx) in Eq. (2) and an adding circuit 411 produces x+n·Δx. If this signal is applied to the address register 209 in FIG. 2, the memory 208 in FIG. 2 supplies f(x+n·Δx) to a multiplying circuit 412. A memory 413 for weighting function is supplied with an address from the counter 410, and when the contents of the counter 410 is n·Δx, the weighting function W(n) is produced from the memory 413. This value is multiplied by f(x+n·Δx) at the multiplying circuit 412, with Eq. (2) being calculated. A setting terminal $I_L$ is for inputting the value of L. The operation of the arithmetic unit in FIG. 4 is performed at the following steps (a) to (f):

(a) Specify l at the position setting device 401.
(b) Reset the counters 403 and 404.
(c) Change n·Δx at the counter 410.
(d) Calculate ΣW(n)·f(x+n·Δx) at the multiplying circuit 412.
(e) Change by 1 the contents of the counter 403 and perform the calculations at steps (a) to (d).
(f) Increment by 1 the contents of the counter 404 after the counter 403 has counted a predetermined number, and perform the calculations at steps (a) to (e).

According to this invention, the radiation source and the radiation detector are combined with the devices for storing and processing the electrical signals from the detector, and while the radiation source and detector are relatively being moved, plural radiation images are measured or photographed, thereby measuring a cross-sectional image on any cross-section of an object to be examined.

We claim:

1. A radiation-image photographying apparatus comprising:
   a radiation source;
   a radiation detector disposed in opposition to said radiation source for detecting radiation through an object to be examined;
   scanning means for changing the relative, positional relationship between said radiation source and said radiation detector with respect to said object and for obtaining a plurality of measurements of a two-dimensional radiation absorption distribution of said object with a fixed image detecting field while said scanning means is changing the relative positional relationship between said radiation source and said radiation detector;
   memory means for storing the plurality of measurements; and
   arithmetic means for arithmetically processing the output from said memory means; said arithmetic means performing a linear arithmetic operation on the plurality of measurments of said radiation passing a point within said object so as to provide an output representative of any cross-sectional image of said object parallel to the plane of said radiation detector.

2. A radiation image photographing apparatus according to claim 1, wherein said radiation detector is formed of an X-ray image intensifier and an image pickup tube for converting a light image obtained from said X-ray image intensifier to an electrical signal.

3. A radiation-image photographing apparatus according to claim 1, further comprising display means for displaying the results of the operation of said arithmetic means.

4. A radiation-image photographying apparatus according to claim 1, wherein said arithmetic means performs the linear arithmetic operation by adding measurements of said radiation passing said point to values obtained by multiplying a predetermined weighting function by measurements of said radiation passing points adjacent to said point.

* * * * *